United States Patent [19]
Turner et al.

[11] Patent Number: 5,912,177
[45] Date of Patent: Jun. 15, 1999

[54] STEM CELL IMMOBILIZATION

[75] Inventors: Marc Leighton Turner, South Queensferry; William Gerrard Murphy, Edinburgh, both of United Kingdom

[73] Assignee: Common Services Agency, Edinburgh, United Kingdom

[21] Appl. No.: 08/765,315

[22] PCT Filed: Jun. 15, 1995

[86] PCT No.: PCT/GB95/01389

§ 371 Date: Apr. 8, 1997

§ 102(e) Date: Apr. 8, 1997

[87] PCT Pub. No.: WO96/00782

PCT Pub. Date: Jan. 11, 1996

[30] Foreign Application Priority Data

Jun. 29, 1994 [GB] United Kingdom .................... 9413029

[51] Int. Cl.⁶ .............................. C12N 15/63; C12N 5/08; C12N 5/10; A61J 1/10
[52] U.S. Cl. ................. 435/455; 435/374; 435/378; 435/397; 435/402; 435/405; 435/408; 435/307.1; 435/308.1; 604/408
[58] Field of Search .................. 435/172.1, 374, 435/378, 397, 402, 405, 408, 455, 307.1, 308.1; 604/408

[56] References Cited

FOREIGN PATENT DOCUMENTS

| | | |
|---|---|---|
| 63-196286 | 8/1988 | Japan . |
| WO 96/16116 | 10/1991 | WIPO . |
| WO 9603160A1 | 2/1996 | WIPO . |

OTHER PUBLICATIONS

Weinstein, R et al. Blood. 73(1): 111–116, Jan. 1989.
Long, MW and Dixit, VM et al. Blood. 75(12): 2311–2318, Jun. 15, 1990.
Long, MW et al. J. Clin Invest. 90: 251–255, Jul. 1992.
Hosokawa, T e tal. Oncology Research. 5(4–5): 183–189, Apr. 1993.
Sekhsaria, S et al. Proc. Nat. Acad. Sci. (USA). 90(16): 7446–7450, Aug. 15, 1993.
Lemoli, RM et al. Exp. Hematology. 20(5): 569–575, Jun. 1992.
Lebkowski, JS et al. Transplantation. 53(5): 1011–1019, May 1992.
Stephen G. Emerson; "The Stem Cell Model of Hermatp-poiesis", In Hoffman, R., Benz, EJ, Shattil SJ, Fune, B., Cohen, HJ (Eds); *Haematology. Basic Principles and Practice: Churchill Living,* NY (1991); pp. 72–81.

*Primary Examiner*—David Saunders
*Assistant Examiner*—F. Pierre VanderVegt
*Attorney, Agent, or Firm*—Lahive & Cockfield, LLP

[57] ABSTRACT

Haematopoietic stem cells (which term includes early progenitor cells) are immobilized on a substrate coated with a fibrin matrix and including a substance capable of both binding to the fibrin matrix and also having an RGD amino acid sequence for binding to the stem cells. The substance may be fibronectin or thrombospondin. The substrate is generally in the form of a closed bag formed of a carbon dioxide-permeable and oxygen-permeable plastics material which allows culturing of the stem cells. The cultured stem cells may re-engraft a patient following chemotherapy or to correct haemotological deficiencies. Stem cells may be harvested from peripheral blood onto the coated substrate. The stem cells in contact with the coated substrate are good candidates for gene therapy to introduce a heterologous gene e.g. employing a transfection vector.

18 Claims, No Drawings

STEM CELL IMMOBILIZATION

TECHNICAL FIELD

The present invention relates to a system for selectively immobilizing stem cells, for example those from the haematopoietic progenitor compartment (HPC). This allows stem cells to be selectively harvested free of other cell types, whereby the harvested cells may be cultured or otherwise manipulated.

BACKGROUND

Stem cells are primitive cells which are capable of self-renewal, and ultimately become differentiated into specific cell types of defined function. Stem cells are capable of proliferation either to generate further identical stem cells, or to produce more differentiated cell types. Later more differentiated cell types always become more differentiated on proliferation. Stem cells exist for most tissue types but are continuously active in the skin and mucosal systems, and for the blood and bone marrow (haematopoietic stem cells).

Haematopoietic stem cells are capable of self-renewal, multilineage proliferation and differentiation, and long-term support of the haematopoietic and lymphoid systems. They form a subpopulation within the Haematopoietic progenitor compartment (HPC), which mainly comprises cells of more limited potentiality. HPC cells are mainly located within the bone marrow stroma, where complex interaction with stromal cells, extracellular matrix components and cytokines, permits regulation of cell proliferation and differentiation. HPC cells are also present in the blood under a variety of physiological, pathological and iatrogenic circumstances. HPC can be harvested from bone marrow or peripheral blood, and will re-engraft the bone marrow following intravenous infusion in patients who have received ablative (i.e. destructive) doses of chemotherapy and/or radiotherapy, leading to regeneration of haematopoiesis and immunity. Thus, HPC cell transplantation is of considerable clinical utility in the management of patients with haematological and solid malignancies, bone marrow failure, and inborn errors of haematopoiesis, immunity or metabolism.

There is thus a need for supplies of autologous HPC cells which may be cultured in vitro prior to reintroduction into a patient whose HPC cell population has been depleted due to chemotherapy and/or radiotherapy. The populations of such HPC cells may take many weeks or months to recover naturally to their normal levels. The use of autologous cells from the patient himself avoids rejection of the transplanted cells. An object of the present invention is to address the culturing of such HPC cells in a convenient manner. This is carried out with a view to improving the rate and durability of haematopoietic recovery, the removal of any neoplastic contamination, and the possible use of HPC calls as a vehicle for immunotherapy and gene therapy.

In vivo, HPC cells are generally located within the bone marrow stroma. In vitro, HPC cells are able to adhere to bone marrow stromal layers before proliferating and releasing more committed progenitors. Stem cells undergo marked proliferation and differention into multiple lineages, ultimately giving rise to fully differentiated cells, such as red blood cells, platelets, a variety of white blood cells, and also immune cells such as T lymphocytes and B lymphocytes. Thus, the reintroduction of HPC cells or stem cells into the patient who is depleted therein, allows efficient repopulation of these haematopoietic cell types.

Although stromal layers may provide a suitable substrate for HPC cell immobilization and culture, such stromal layers have a number of disadvantages. Firstly they are fragile. This imposes limitations on the types of systems which may be employed to culture such cells. The growth of HPC cells in vitro requires a rigid substrate on which the layers of stromal cells can be grown in order to maintain the integrity of the stroma. Moreover, it is found that HPC cells grown on stroma in this way only have a limited storage lifetime, of about six to eight weeks due to death of the stromal cells. A further problem is that the use of the stromal cells for the growth of HPC cells is limited to HPC cells derived from bone marrow, and cannot be used to culture other HPC cell types, such as mucosal cells.

In the case of an autologous graft, there may be a need to culture HPC cells for re-engrafting using stromal cells which are also derived from the patient himself. Immunological problems of rejection may arise if non-autologous stromal cells are used to culture the stem cells. The need to first collect and then grow a layer of the patient's stromal cells before they can be used to culture his HPC cells adds to the time and complexity of the production of the autologous HPC cells. In the case of bone marrow, a sample thereof contains not only stem cells but also the required stromal cells. However, if stem cells are harvested from peripheral blood or cord blood stromal cells are absent and have to be provided from a non-autologous source, leading to possible immunological problems.

Finally, the stromal cultures contain an ill-defined set of cells, growth factors etc. which renders the controlled culturing thereof very difficult if reproducible stromal cultures or predictable characteristics are to be obtained.

It is an object of the present invention to mitigate these problems.

SUMMARY OF THE INVENTION

Broadly speaking, the present invention resides in the discovery that a suitable substrate, such as a plastics material, can be coated with a fibrin matrix together with a substance capable of binding stem cells such as fibronectin, and that this will in turn selectively bind stem cells and allow culturing and manipulation thereof. Thus, the use of stromal cells may be avoided.

Specifically, one aspect of the present invention provides a system for selectively immobilizing stem cells, for example, those from the haematopoietic progenitor compartment (HPC), which comprises a substrate having a coating comprising a fibrin matrix, together with a substance capable of binding to the fibrin matrix and having a binding site for binding an RGD amino acid sequence for binding to the stem cells.

The binding substance capable of binding to the fibrin matrix and also having an ROD amino acid sequence may be a blood clotting factor such as fibronectin or thrombospondin or mixtures thereof, both of which bind to fibrin and also selectively bind stem cells via the RGD binding site on the binding substance. Alternatively the binding substance may be a synthetic molecule which includes an RGD sequence.

The specificity of binding of stem cells to a binding substance such as fibronectin allows the stem cells to be selectively immobilized on the substrate where they can be cultured or otherwise manipulated. This allows a variety of substrates including non-rigid flexible substrates which would not otherwise bind stem cells, to be employed.

In fact, in addition to stem cells early progenitor cells may also immobilise on the substrate so that these may also be selectively immobilized (and are included in the definition of the term "stem cells"). However, late progenitor cells will not adhere to the coating on the substrate. Early progenitor cells retain some ability for multilineage proliferation, whereas late progenitor cells are generally restricted to a single lineage.

The nature of the substrate will vary dependent on the manipulations which are to be carried out on the immobilized stem cells. For example, selective binding of stem cells to the substrate allows for separation of stem cells from neoplastic cells. Thus, re-engrafted material may be freed from neoplastic cells prior to reintroduction into the patient so as to avoid a recurrence of the cancer.

Moreover, the immobilized stem cells may function as a target for gene transfection. There is evidence which suggests that incubation of HPC stem cells with fibronectin fragments improves the frequency of gene transfection using retroviral vectors. Such gene therapy generally involves the introduction of a gene either to introduce a new gene or to correct a genetic deficiency. Such therapy may be used to treat congenital defects of haemopoiesis, immunity and metabolism, or as a cancer therapy.

The invention thus avoids the use of layers of stromal cells, which require a rigid substrate to maintain their integrity.

Whilst it may be possible to culture stem cells in suspension, this tends to lead to early differentation of the cells; whereas the culturing of stem cells adhered to a substrate may allow early differentation to be avoided. Generally, we prefer to maintain a high population of stem cells for re-engrafting, which may then differentiate according to the patient's requirements in vivo.

A particularly preferred embodiment of the present invention, employs a closed container, such as a plastics bag formed of a flexible plastics material such as that of the type normally used in blood bags and which is gas permeable to carbon dioxide and oxygen so as to allow cell culture within the bag. However, such blood-bag plastics materials whilst suitable from the gas permeability point of view, are designed so as to be non-adherent to normal blood cell types so as to avoid the undesirable retention of blood cells on the inside of the bag. Moreover, such plastics materials conventionally include plasticiser materials and other reagents which may prove toxic or inhibitory to stem cell replication. Finally, the optical properties of such bags are preferably such as to allow the development of optical or spectoscopic cell and infection monitoring systems, thereby reducing the need for sub-sampling.

It is surprisingly found according to the present invention that such bags can be effectively coated with fibronectin or other binding substance, such that the fibronectin forms part of an adherent coating over the plastics surface, by employing a fibrin matrix which adheres to the plastics surface. Furthermore, it is surprisingly found that the stem cells are able to grow on the coating of fibronectin or other binding substance. This enables the advantageous culturing of autologous stein cells within sterile closed plastics containers, such as bags intended for blood storage. Procedures for handling and storing such bags are well established. Suitable bags are available from Tuta Laboratories (Australia) Pty Ltd., Sydney, Australia, under the trademark TUTA CLX. Suitable plastics materials include polystyrene and polyvinylchloride, which are often plasticised with TEHTM (tri(2-ethylhexyl)trimellitate) or DEHP (di(2-ethylhexyl)phthalate. Other suitable plastics materials are available from Baxter Health Care Ltd., Newbury, United Kingdom.

The use of a sealed plastics bag, such as those currently used for storing blood provides a convenient vehicle for culturing stem cells. Advantages include maintenance of sterility, reduced operator exposure to potential hazards from the cell harvest, and also from any reagents used during manipulative operations on the cultured cells.

Another important feature of the invention is not only the ability to selectively bind stem cells onto the coating of fibronectin or other binding substance, but also to allow their removal thereof at a chosen time. Suitable methods include the use of divalent cation chelation and competitive removal using RGD-containing peptides which will compete for the stem cell binding sites on fibronectin.

The limited ability of fibronectin or other binding substance to bind to the substrate is substantially enhanced by coating the substrate with a fibrin matrix. In a preferred embodiment, the fibrin matrix is produced in situ by the reaction of fibrinogen with thrombin whereby fibrin is deposited. The coating procedure may include the preliminary coating of the substrate with a fibrin matrix, followed by deposition thereon of fibronectin. Alternatively, the fibronectin may be incorporated into the fibrin matrix by depositing a mixture of fibrinogen and fibronectin on the substrate followed by treatment with thrombin to convert fibrinogen to fibrin in situ. In fact, fibrinogen is commonly available from lyophilised cryoprecipitate (obtained during blood protein fractionation) which also contains amounts of fibronectin. Fibrin-fibronectin coatings show good stem cell adhesion.

The fibrin matrix is also capable of being sterilised by conventional sterilisation techniques without substantial degradation.

A benefit of the system according to the present invention when used for culturing stem cells, is that it has general applicability to stem cells of all types, that is to say skin, mucosal, blood and marrow types (including HPC cells). In contrast, the use of layers of stromal cells to culture stems cells is applicable only to HPC cells derived from blood and bone marrow.

The coating may include other factors which nay assist the selection, culturing or release of the stem cells. For example, proteoglycans such as heparan sulphate, immobilized cytokines or modified monoclonal antibodies may be included. The binding selectivity of the coating may be enhanced by the inclusion of monoclonal antibodies directed to unique stem cell surface markers such as CD34, or antibodies which include an RGD binding site. The coating may include agents which will specifically bind and kill neoplastic cells. The skilled man will be aware of the need to provide other factors to enable the culturing of the immobilized stem cells.

DESCRIPTION OF PREFERRED EMBODIMENTS

Embodiments of the present invention will now be described by way of example only.

EXAMPLE 1

Cell Adhesion Molecule Expression by Human Haematopoietic Cell Line KGla

In order to validate the use of cell line KGla as a model system for HPC cells (including HPC stem cells), we characterised the pattern of cell adhesion molecule expression on HPC cells derived from normal bone marrow and peripheral blood following mobilisation with high-dosage cyclophosphamide and recombinant human granulocyte colony stimulating factor, and compared it with expression from KGla. Samples were separated by Ficoll discontinuous density-gradient centrifugation. The mononuclear cell layer was removed, and the cells washed twice in a handling medium (phosphate buffered saline [PBS] containing 1% bovine serum albumin, 0.1% sodium azide and 0.02% ethylene diaminetetra-acetic acid [EDTA]). The cells were incubated for 15 min in 0.1% human gamma globulin (Sigma) in PBS to effect Fc receptor blockade. Aliquots of $5 \times 10^5$ cells per test were incubated with purified monoclonal antibody to one of a panel of cell adhesion molecules (Table I) for 15 min. The cells were washed twice in handling medium, and incubated with the second step reagent —a sheep anti-mouse R-phycoerythrin conjugate (Sigma), again for 15 mins. The cells were washed again, incubated for 15 min with mouse serum, to blockade the second-step reagent, and then incubated with the third step reagent—an anti-CD34 monoclonal antibody directly conjugated to fluorescein isothiocyanate (BG12-FITC, Becton Dickinson). The CD34 cell surface antigen identifies the HPC cells (which typically constitute only about 1% of the total cells). The cells were washed a final time, and fixed in 2% paraformaldehyde (Sigma) in PBS, prior to analysis. Appropriate control samples were established using monoclonal antibodies to CD45 as a positive control, and an isotype-specific antibody of irrelevant specificity as negative control, appropriately stained with each fluorochrome.

30–50,000 cells were acquired through a lymphoblastoid acquisition gate using a FACScan flow cytometer (Becton Dickinson), with prior standardisation of the instrument settings and two-colour compensation using control samples. Data was acquired and analysed using Lysis II software (Becton Dickinson). We demonstrated expression of ICAM-1, PECAM-1, LFA-3, LFA-1, VLA-4, VLA-5, L-Selectin and HCAM (Table II). Peripheral blood HPC demonstrated a similar pattern of expression, except in that there was less expression of LFA-3, and VLA-5. VLA-4 and VLA-5 are members of the $B_1$ integrin family, and recognise and adhere with high-avidity to fibronectin. L-Selectin recognises carbohydrate moieties such as Sialyl Lewis X, with low avidity binding. HCAM recognises collagen type 1 and hyaluronic acid. The lower levels of VLA-5 expression by circulating progenitors is suggestive that the VLA-5: fibronectin adhesion pathway may be instrumental in mediating HPC-stromal adhesion.

In view of the problems associated with obtaining highly purified human HPC populations, we therefore utilised the primitive human haematopoietic cell line KGla as a model early progenitor during development of a binding assay. Dual immunocytometry revealed KGla to be CD34 positive, and to express a similar cell adhesion molecule profile to normal haematopoietic progenitors (Table II).

EXAMPLE 2

Development of a Functional Binding Assay to Assess Adhesion of Haematopoietic Progenitors to Extracellular Matrix Components We explored the functional binding of KGla to a panel of bone extracellular matrix components using a $^{51}$ chromium radiolabelling assay adapted from the work of Cheryl Hardy and Jose Minguell (1993). $1 \times 10^7$ KGla were incubated with 200 kBq $^{51}$chromium (Amersham International) in 100 µl of foetal calf serum [FCS] for 1 hr. and washed twice in large volumes of Iscove's Modified Dulbecco's Medium [IMDM], with 10% FCS. The radiolabelled cells were aliquoted at a concentration of $2 \times 10^5/200$ µl, and dispensed into 2cm² wells of a 24 well flat-bottomed tissue culture dish (Costar). The wells were prior coated with extracellular matrix components known to be present in bone marrow stroma (Gordon, 1988; Clark, Gallagher & Dexter, 1992) (Table III). 100 µl of a solution containing 100 µg/ml (collagens) in 0.1% acetic acid in distilled water, or 50 µg/ml (fibronectin and proteoglycans) in distilled water, was added to each well and allowed to dry in a 37° C. oven for 1 hr. 1% denatured bovine serum albumin (Sigma) was used to coat negative control wells. The cells were incubated with the substrate for 2 hrs at 37° C., and the supernatant removed. The wells were washed twice with IMDM 10% FCS, and the washes and supernatant added to a scintillation vial. 0.5 ml of 0.1% Non-Idet in distilled water was added to each well for 15 min to lyse the adherent cells. This was also removed into a scintillation vial. Both adherent and non-adherent fractions were counted for 30 min in a Hewlett-Packard Gamma Counter, and the percentage binding calculated. Each assay was carried out in triplicate within each plate, and the mean percentage binding calculated. This assay system was standardised, and its reproducibity demonstrated. KGla were found to bind to tissue culture grade plastics (for comparison purposes), but not to TUTA CLX blood-bag plastic. The former was blocked by coating the well with denatured BSA or other proteins. KGla bound significantly to plasma and tissue fibronectin, but not to various collagens or proteoglycans (Table IV). Percentage adherence to fibronectin was remarkably constant over a range of cell concentrations between $1 \times 10^4$ to $2 \times 10^6$ cells per 2cm² well, but fell sharply at $1 \times 10^7$ cells/well, consistent with a maximal binding capacity of 430,000 cells/cm². Whether the maximal binding capacity is a reflection of saturation of fibronectin binding sites or of steric hinderance is currently unclear. Binding was abrogated at 4° C., but stable at room temperature and 37° C. The use of various incubating media (IMDM or RPMI, with and without FCS) made no difference to binding. In addition, binding reached a plateau after 1 hr, with no benefit to prolonged incubation periods. Fibronectin binding could be abrogated by carrying out the substrate incubation in a medium from which divalent cations had been removed (Hanks Balanced Salts Solution (Northumbria Biologicals) with 10 mmol EDTA (p,0.01), or in a 3 mmol solution of an arginine-glycine-asparatate-serine peptide (Sigma) in IMDM (p,0.01), though not in a solution of IMDM with 3 mmol of a control peptide (arginine-glycine-glutamate-serine) (Sigma). Finally, it was found that it made no difference to the % KGla binding whether the fibronectin was dried onto the well surface, or simply incubated at room temperature for 1 hr.

EXAMPLE 3

Optimal Coating TUTA CLX Blood Bag Plastic with Fibronectin

The possibility of coating a flexible plastics material was investigated. A TUTA CLX blood bag was cut open along the side seams, and a section of one side wag clamped in a Bio-Dot (Bio-Rad) dot blot apparatus so that the inner bag surface was exposed at the bottom of the 96 wells of the apparatus (96 well plate layout). Human plasma fibronectin [pFN] (Sigma) and tissue fibronectin [tFN] derived from foreskin fibroblasts (Sigma) were dissolved in pyrogen-free water to give a stock solution at 500 µg/ml. 50 µl of doubling dilutions of the pFN and tFN solutions were added across well columns 1–11. Column 12 contained water only (control). After 1 hr at room temperature, the well contents were removed, and the wells were washed 4 times with pyrogen-free water. Rabbit polyclonal anti-plasma fibronectin [RPpFN] (Sigma) and mouse monoclonal anti-tissue fibronectin [MMtFN] (Sigma) were diluted 1:500 in buffer 1 (phosphate buffered saline (pH 7.2) containing 0.1% Tween 20, and 0.05% sodium azide), and 50 µl was added to each well of the microplate. After 90 min. at room temperature the well contents were removed, and wells were washed with buffer 2 (phosphate buffered saline (pH 7.2) containing 0.1% Tween 20, 0.05% sodium azide, 1% bovine serum albumin, and 4% polyethylene glycol). Alkaline phosphatase conjugated goat anti-rabbit 1gG [APaR] (zymed) and alkaline phosphatase conjugated rabbit anti-mouse Ig [APaM] were diluted 1:1200 in buffer 2. 50 µl was added to the appropriate well series, and after 120 min at room temperature the well contents were removed, and the wells washed 5 times with buffer 2 and a further thrice with pyrogen-free water. The top manifold of the Bio-Dot apparatus was unclamped, and washed with sodium hydroxide, detergent (Decon) and distilled water to remove/destroy any of the above reagents which may have attached to the manifold. The manifold was clamped back into position over the sheet of blood bag plastic, and alkaline phosphatase substrate solution (Sigma) added at 140 µl per well. Colour could be seen to be developing at the well bottom, at the blood bag surface. The apparatus was left on an orbital mixer for 40 min at room temperature, 100 µl was transferred from each well to a half area microplate (Costar), and the optical density was read at 405 nm (minus 650 nm reference). The results are illustrated graphically in FIG. 1. There was some background binding or the alkaline phosphatase labelled anti Ig antibodies (APaR and APaM) to fibronectin alone (3,6). The anti-tissue fibronectin antibody (MMtFN) showed relatively weak selective binding to pFN (2), and only slightly better binding to tFN (4). This may be a reflection of the particular concentrations of the anti-tFN antibody (MMtFN) and the anti-mouse Ig antibody (APaM) used in this experiment. The anti-pFN antibody (RPpFN) showed strong selective binding to both pFN (1) and tFN (5), and showed that binding of tFN to the plastic surface was superior to that of pFN at lower concentration ranges (0.5 to 8 µg/ml). Both pFN and tFN achieved saturation binding at approximately 20 µg/ml, but showed some evidence of "prozone" above approximately 50 µg/ml, i.e. there was some decrease in binding suggesting less firm anchorage of fibronectin to plastic at higher coating concentrations. This usually suggests multivalency of binding, such that more valencies are used at lower concentrations to establish firm binding while at higher concentrations there is competition for binding sites, less valencies are occupied, and the reagent is more readily detached.

EXAMPLE 4

Binding of KGla to Fibronectin Coated TUTA CLX Blood-Bag Plastic

It proved necessary to adapt the $^{51}$chromium adhesion assay in order to examine KGla (used as a model for HPC cell binding) adhesion to TUTA CLX blood-bag plastic. The base of a 24 well plate was removed, a blood-bag cut open, and the internal surface adhered to the base of the plate. Care was taken to ensure that adhesive did not spread onto the test surface, and that a water-seal was achieved around each well individually. Wells were tested for continence with 1 ml of distilled water.

In an initial series of experiments, KGla adhesion was examined to the plastic itself, following coating with plasma or tissue fibronectin, or following coating with BSA. The results are summarised in Table V. KGla showed no significant binding to any of wells under these conditions, and we suspect that the negligable charge on the surface of the blood-bag plastic leads to only a very loose coating with fibronectin.

We considered a number of options to increase the extent and avidity of fironectin binding, including pre-coating the surface with a fibrin glue. Fibrin glue consists of two proteinaceous compounds, which form an adhesive matrix on reconstitution and mixing. one component is prepared from cryoprecipitate obtained from a large pool of voluntary UK blood donations. The material is lyophilised and subjected to heat treatment (80° C. for 72 hrs) to minimise the risk of viral transmission. The lyophilised croprecipitate consists mainly of fibrinogen (225 mg/vial) and factor XIII (50 units/vial), but probably also small amounts of other plasma proteins such as fibronectin, thrombospondin and von Willebrand's factor. The solvent for this component is water containing 20 mM Tris buffer (pH 7.5), and aprotinin (Trasylol, Bayer) at 3,000 kallikrein inactivator units/ml. The latter acts as a proteolytic enzyme inhibitor. The second component is lyophilised human thrombin, at 1000 IU/vial, reconstituted with a solution of 4 mM calcium chloride. When the two components are mixed, the thrombin activates the fibrinogen to fibrin, and also activates factor XIII to factor XIIIa, which stabilises the fibrin though cross-linking. Other proteins which may be present (such as fibronectin) will also be cross-linked into the matrix by factor XIIIa.

We coated TUTA CLX blood-bag plastic with fibrin matrix alone, fibrin matrix onto the surface of which plasma fibronectin had been incubated using the standard protocol (fibronectin contains fibrinogen binding domains), and fibrin matrix into which fibronectin had been added (to the fibrinogen component at 0.05 mg/ml) such that the fibronectin was cross-linked into the matrix by factor XIIIa. The results are tabulated in Table V.

TABLE I

| Cell adhesion molecules studied. | | |
|---|---|---|
| Cytoadhesion molecule (CD) | Ligand | Monoclonal Antibody (Source) |
| Immunoglobulin Gene Superfamily. | | |
| ICAM-1 (CD54) | LFA-1 | 84HIO (Immunotech) |
| PECAM-1 (CD31) | | 5.6E (Immunotech) |
| LFA-3 (CD58) | LFA-2 | AICD58 (Immunotech) |
| Integrin Family. | | |
| $\beta_1$ VLA subfamily. | | |
| VLA-4 (CDw49d/CD29) | Fibronectin | HP2/1 (Immunotech) |
| VLA-5 (CDw49e/CD29) | Fibronectin | SAM1 (Immunotech) |
| $\beta_2$ leukocyte adhesion subfamily | | |
| LFA-1 (CD11a/CD18) | ICAM1/2 | IOT16 (Immunotech) |
| $\beta_3$ cytoadhesion subfamily. | | |
| Vitronectin receptor (CD51/CD61) | Vitronectin | AMF7 (Immunotech) |
| Selectin Family. | | |
| L-Selectin | Carbohydrate | Dreg56 (Immunotech) |
| Proteoglycan Analogues. | | |
| HCAM (CD44) | Collagen Hyaluronic Acid | F10-44-2 (Serotech) |
| CD36/LIMP II Family. | | |
| Thrombospondin receptor (CD36) | Collagen Thrombospondin | FA-152 (Immunotech) |

TABLE II

Cell adhesion molecule expression.

| Adhesion molecule | Bone Marrow | Peripheral Blood | KG1a. |
|---|---|---|---|
| ICAM-1 (CD54): | 91 ± 11% | 93 ± 11% | 98.6 ± 3% |
| PECAM-1 (CD31): | 91 ± 7% | 94 ± 6% | 30 ± 13% |
| LFA-3 (CD58): | 65 ± 25% | 27 ± 18% | 98 ± 1% |
| LFA-1 (CD11a): | 84 ± 12% | 78 ± 15% | 99 ± 1% |
| VLA-4 (CDw49d): | 67 ± 25% | 71 ± 23% | 99 ± 3% |
| VLA5-(CDw49e): | 62 ± 19% | 32 ± 19% | 99 ± 3% |
| VNR (CD51): | 9 ± 7% | 5 ± 6% | 7 ± 3% |
| L-Selectin: | 64 ± 22% | 60 ± 28% | 5 ± 4% |
| HCAM (CD44): | 98 ± 2% | 97 ± 5% | 99 ± 0.5% |
| CD36: | 20 ± 11% | 14 ± 14% | 35 ± 13% |

TABLE III

Extracellular matrix components studied.

Collagen Type I, acid soluble from human placenta. (Sigma, Type VIII)
Collagen Type III, acid soluble from human placenta. (Sigma, Type X).
Collagen Type IV, acid soluble from human placenta. (Sigma, Type VI)
Fibronectin, from human plasma. (Sigma).
Fibronectin, from human foreskin fibroblasts. (Sigma).
Heparan Sulphate, sodium salt from bovine kidney. (Sigma).
Chondroitin Sulphate A. sodium salt from bovine trachea. (Sigma).
Hyaluronic Acid, from human umbilical cord. (Sigma).
(Gordon, 1988; Clark, Gallagher & Dexter, 1992)
Thrombospondin.

TABLE IV

KG1a binding to extracellular matrix components.

| | |
|---|---|
| denatured albumin | 8.3 ± 5.1% |
| collagen type I | 5.2 ± 1.7% |
| collagen type III | 10.1 ± 7.9% |
| collagen type IV | 4.3 ± 2.1% |
| heparan sulphate | 4.5 ± 1.2% |
| chondroitin sulphate | 5.2 ± 1.7% |
| hyaluronic acid | 6.9 ± 1.3% |
| plasma fibronectin | 28.3 ± 5.2% |
| thrombospondin | 76.2 ± 12.8% |

TABLE V

KG1a binding to TUTA CLX blood-bag plastic.

| substrate | mean % adherence ± 1 standard error | (number of experiments) |
|---|---|---|
| plastic | 7.5 ± 2.3% | (3) |
| plasma fibronectin | 7.4 ± 0.5% | (3) |
| tissue fibronectin | 7.5 ± 1.9% | (2) |
| bovine serum albumin | 5.0 ± 1.2% | (2) |
| fibrin matrix | 22.9% | (1) |
| fibrin matrix + pFn (coated) | 38.9% | (1) |
| fibrin matrix + pFn (inclusive) | 32.5 ± 16.1% | (3) |

REFERENCES

Clark B. R., Gallagher J. T., Dexter T. M. (1992). Cell adhesion in the stromal regulation of haemopoiesis. In: Lord B. I., Dexter T. M., eds. Growth Factors in Haemopoiesis; Clinical Haematology 5 (3). London: Balliere Tindall, 617–652.

Coulombel L., Vuillet M. H., Leroy C., Tchernia G. (1988). Lineage and stage specific adhesion of human hematopoietic progenitor cells to extracellular matrices from fibroblasts. Blood 71: 329–334.

Dexter T. M., Allen T. D., Lajtha L. G. (1977). Conditions controlling the proliferation of hematopoietic stem cells in vitro. Journal of Cellular Physiology 91: 335–344.

Giancotti F. G., Comoglio P. M., Tarone G. (1986). Fibronectin-plasma membrane interaction in the adhesion of hemopoietic cells. Journal of Cell Biology 103: 429–437.

Gordon M. Y., Dowding C. R., Riley G. P., Goldman J. M., Greaves M. F. (1987). Altered adhesive interactions with marrow stroma of haematopoietic progenitor cells in chronic myeloid leukaemia. Nature 328: 342–344.

Gordon M. Y., Riley C. P., Watt S. M., Greaves M. F. (1987). Compartmentalization of a haematopoietic growth factor (GM-CSF) by glycosaminoglycans in the bone marrow microenvironment. Nature 326: 403–405.

Gordon M. Y., Piley G. P., Clarke D. (1988). Heparan sulfate is necessary for adhesive interactions between human early hemopoietic progenitor cells and the extracellular matrix of the marrow microenvironment. Leukaemia 2: 804–809.

Gordon M. Y. (1988). Extracellular matrix of the marrow microenvironment. British Journal of Haematology 70: 1–4.

Hardy C. L., Minguell J. J. (1993). A cytoadhesion assay for the binding of cloned hemopoietic progenitor cells to stroma. Experimental Hematology 1993; 21: 283–288.

Hynes R. O. (1990). Fibronectins. New York: N.Y. Springer Verlag.

Lemoli R. M., Tafuri A., Strife A., Andreeff M., Clarkson B. D., Gulati S. C. (1992). Proliferation of human hematopoietic progenitors in longterm bone marrow cultures in gas-permeable plastic bags is enhanced by colony-stimulating factors. Experimental Hematology 20: 569–575.

Moritz T., Patel V., Williams D. A. (1993). Bone marrow matrix molecules (BMMM) increase efficiency of retroviral mediated gene transfer (RMGT) into hematopoietic cells. Experimental hematology 21: 1027.

Piersbacher M. D., Ruoslahti E. (1984). The cell attachment activity of fibronectin can be duplicated by small synthetic fragments of the molecule. Nature 309: 30–33.

Saeland S., Duvert V., Caux C., Pandrau D., Favre C., Valle A., Durand I., Charbord P., de Vries I., Banchereau J. (1992). Distribution of surface-membrane molecules on bone marrow and cord blood CD34+ hematopoietic cells. Experimental Hematology 20; 24–33.

Tsai S., Patel V., Beaumont E., Lodish H. F., Nathan D. G., Sieff C. A. (1987). Differential binding of erythroid and myeloid progenitors to fibroblasts and fibronectin. Blood 69; 1587–.

Turner M. L., McIlwaine K., Anthony R. S., Parker A. C. (1993). Cytoadhesion molecule expression by human haematopoietic progenitor cells from bone marrow, peripheral and cord blood. Experimental Hematology 21: 1069.

Verfaille C., Blakolmer K., McGlave P. (1990). Purified primitive human haematopoietic progenitor cells with long-term in vitro repopulating capacity adhere selectively to irradiated bone marrow stroma. Journal of Experimental Medicine 172: 509.

Verfaille C. M., McCarthy J. B., McGlave P. B. (1990). Differentiation of primitive human multipotent hematopoietic progenitors into single lineage clonogenic progenitors is accompanies by alterations in Medicine 174: 693.

Vuillet-Gaugler M. H., Breton-Gorius J. Vainchenker W., Guichard J., Leroy C., Tchernia C., Coulombel L. (1990). Loss of attachment to fibronectin with terminal human erythroid differentiation. Blood 75: 865.

Williams D. A., Rios M., Stephens C., Patel V. P. (1991). Fibronectin and VLA-4 in haematopoietic stem cell—microenvironment interactions. Nature 352: 43B.

We claim:

1. A system for selectively immobilizing and culturing stem cells onto the inner surface of a flexible container, the system comprising a closed container formed of a flexible plastic material which is permeable to carbon dioxide and oxygen, the container including a substrate having a coating disposing a fibrin matrix, together with a substance capable of binding to the fibrin matrix and having an RGD amino acid sequence for binding to the stem cells, wherein the container is configured to allow stem cell culture to adhere to the inner surface of the flexible container.

2. A system according to claim 1 wherein the substance capable of binding to the fibrin matrix and also having an RGD amino acid sequence is fibronectin.

3. A system according to claim 1 wherein the substance capable of binding to the fibrin matrix and also having an RGD amino acid sequence is thrombospondin.

4. A system according to claim 1 wherein the fibrin matrix is produced in situ on the substrate by the reaction of fibrinogen with thrombin.

5. A system according to claim 4 wherein the fibrinogen is in the form of cryoprecipitate, which also contains fibronectin.

6. A system according to claim 1 which further comprises a factor selected from the group consisting of proteoglycans, cytokines and monoclonal antibodies.

7. A system according to claim 1 which further comprises a layer of stem cells bound to the coated substrate.

8. The system of claim 1, wherein the closed container is a blood bag.

9. A method of harvesting stem cells from peripheral or cord blood, the method comprising the steps of introducing the blood into a closed container formed of a flexible plastic material which is permeable to carbon dioxide and oxygen, disposing in said container a substrate having a coating including a fibrin matrix, together with a substance capable of binding to the fibrin matrix and having an RGD amino acid sequence for binding to the stem cells, such that the stem cells are selectively immobilized on the substrate and harvested from the blood, and adhering said stem cells to the inner surface of the flexible container.

10. A method of storing and preserving stem cells on the inner surface of a flexible container, which comprises the steps of storing the stem cells in a closed container formed of a flexible plastic material which is permeable to carbon dioxide and oxygen, the closed container including a substrate having a coating including a fibrin matrix, together with a substance capable of binding to the fibrin matrix and having an RGD amino acid sequence for binding to the stem cells such that the stem cells are immobilized on the substrate within the container, and adhering said stem cells to the inner surface of the flexible container.

11. The method of claim 10, wherein the stem cells are from peripheral or cord blood.

12. A method of transfecting stem cells which comprises maintaining the stem cells in a closed container formed of a flexible carbon dioxide-permeable and oxygen-permeable plastic material, the container including a substrate having a coating including a fibrin matrix, together with a substance capable of binding to the fibrin matrix and having an RGD amino acid sequence for binding to the stem cells, such that the stem cells are immobilized on the substrate within the container, and adhering said stem cells to the inner surface of the flexible container;

and transfecting the stem cells with a vector containing a heterologous gene.

13. A method according to claim 12 wherein the vector is a retroviral vector.

14. A method according to any of claims 9, 10, 12, or 13 wherein said substance is fibronectin or thrombospondin.

15. The method of claim 12, wherein the stem cells are from peripheral or cord blood.

16. A method of culturing stem cells in vitro onto the inner surface of a flexible container, which comprises the steps of culturing the stem cells in a closed container formed of a flexible carbon dioxide-permeable and oxygen-permeable plastics material, the container including a substrate having a coating disposing a fibrin matrix, together with a substance capable of binding to the fibrin matrix and having an RGD amino acid sequence for binding to the stem cells, such that the stem cells are immobilized and cultured on the substrate within the container, and adhering said stem cells to the inner surface of the flexible container.

17. The method of claim 16, wherein the coating further comprises a factor selected from the group consisting of proteoglycans, cytokines and monoclonal antibodies.

18. The method of claim 16, wherein the stem cells are from peripheral or cord blood.

* * * * *